(12) United States Patent
Chiou et al.

(10) Patent No.: US 11,782,046 B2
(45) Date of Patent: Oct. 10, 2023

(54) SINGLE-PIXEL OPTICAL TECHNOLOGIES FOR INSTANTLY QUANTIFYING MULTICELLULAR RESPONSE PROFILES

(71) Applicant: The Regents of the University of California, Oakland, CA (US)

(72) Inventors: Pei-Yu E. Chiou, Los Angeles, CA (US); Michael A. Teitell, Tarzana, CA (US); Xiongfeng Zhu, Los Angeles, CA (US); Xing Haw Marvin Tan, Jurong West (SG); Thang Nguyen, Fountain Valley, CA (US)

(73) Assignee: The Regents of the University of California, Oakland, CA (US)

( * ) Notice: Subject to any disclaimer, the term of this patent is extended or adjusted under 35 U.S.C. 154(b) by 430 days.

(21) Appl. No.: 16/626,507

(22) PCT Filed: Jul. 3, 2018

(86) PCT No.: PCT/US2018/040805
§ 371 (c)(1),
(2) Date: Dec. 24, 2019

(87) PCT Pub. No.: WO2019/010234
PCT Pub. Date: Jan. 10, 2019

(65) Prior Publication Data
US 2020/0116696 A1 Apr. 16, 2020

Related U.S. Application Data

(60) Provisional application No. 62/528,405, filed on Jul. 3, 2017.

(51) Int. Cl.
*G01N 33/483* (2006.01)
*G01D 5/26* (2006.01)
(Continued)

(52) U.S. Cl.
CPC ......... *G01N 33/4833* (2013.01); *G01D 5/266* (2013.01); *G01D 5/285* (2013.01); *G01N 33/5008* (2013.01)

(58) Field of Classification Search
CPC .......... G01N 33/4833; G01N 33/5008; G01D 5/266; G01D 5/285
See application file for complete search history.

(56) References Cited

U.S. PATENT DOCUMENTS 6,585,939 B1 7/2003 Dapprich
2014/0080171 A1 3/2014 Gimzewski et al.

FOREIGN PATENT DOCUMENTS

WO WO 2013/090738 A9 6/2013

OTHER PUBLICATIONS

C. L. Lee, M. D. Dawson, and E. Gu, "Diamond double-sided micro-lenses and reflection gratings," Opt. Mater. 32(9), 1123-1129 (2010).*

(Continued)

*Primary Examiner* — Hwa Andrew Lee
(74) *Attorney, Agent, or Firm* — Tom Hunter; Weaver Austin Villeneuve Sampson LLP

(57) ABSTRACT

New platform technologies to actuate and sense force propagation in real-time for large sheets of cells are provided. In certain embodiments the platform comprises a device for the measurement of mechanical properties of cells or other moieties, where device comprises a transparent elastic or viscoelastic polymer substrate disposed on a rigid transparent surface; and a plurality of micromirrors disposed on or in said polymer substrate, wherein the reflective surfaces of the micromirrors are oriented substantially parallel to the surface of said polymer substrate. In certain embodiments the device comprises more than about 1,000,000, or more than about 10,000,000 micromirrors. In certain embodi- (Continued)

ments the micromirrors comprise a magnetic layer and/or a diffraction grating.

16 Claims, 10 Drawing Sheets

(51) Int. Cl.
  *G01D 5/28*   (2006.01)
  *G01N 33/50*   (2006.01)

(56) References Cited

OTHER PUBLICATIONS

PCT International Search Report and Written Opinion dated Sep. 14, 2018 issued in PCT/US2018/040805.
PCT International Preliminary Report on Patentability and Written Opinion dated Jan. 7, 2020 issued in PCT/US2018/040805.
Chiou et al. (2005) "Massively parallel manipulation of single cells and microparticles using optical images" *Nature*, 436(7049): 370-372.
Chun, J. et al. (2012) "Rapidly quantifying drug sensitivity of dispersed and clumped breast cancer cells by mass profiling." *Analyst*, 137: 5495-5498.
Edgar et al. (2019) "Principles and prospects for single-pixel imaging" *Nat. Photonics*, 13: 13-20.
Kung, Y.C. et al. (2015) "Fabrication of 3D high aspect ratio PDMS microfluidic networks with a hybrid stamp." *Lab Chip*, 15: 1861-1868.
Kung, Y.C. et al. (2016) "Tunnel Dielectrophoresis for Tunable, Single-Stream Cell Focusing in Physiological Buffers in High-Speed Microfluidic Flows." *Small*, 12: 4343-4348.
Liu, et al. (2017) "Fabrication strategy for micro soft robotics with semiconductor devices integration," *2017 IEEE 30th International Conference on Micro Electro Mechanical Systems (MEMS)*, pp. 663-666, doi: 10.1109/MEMSYS.2017.7863495.
Zheng et al. (2021) "Dynamic real-time imaging of living cell traction force by piezo-phototronic light nano-antenna array" *Sci. Adv.*, 7: eabe7738 (8 pages).

\* cited by examiner

A. No Force

B. Pressed by a spherical bead

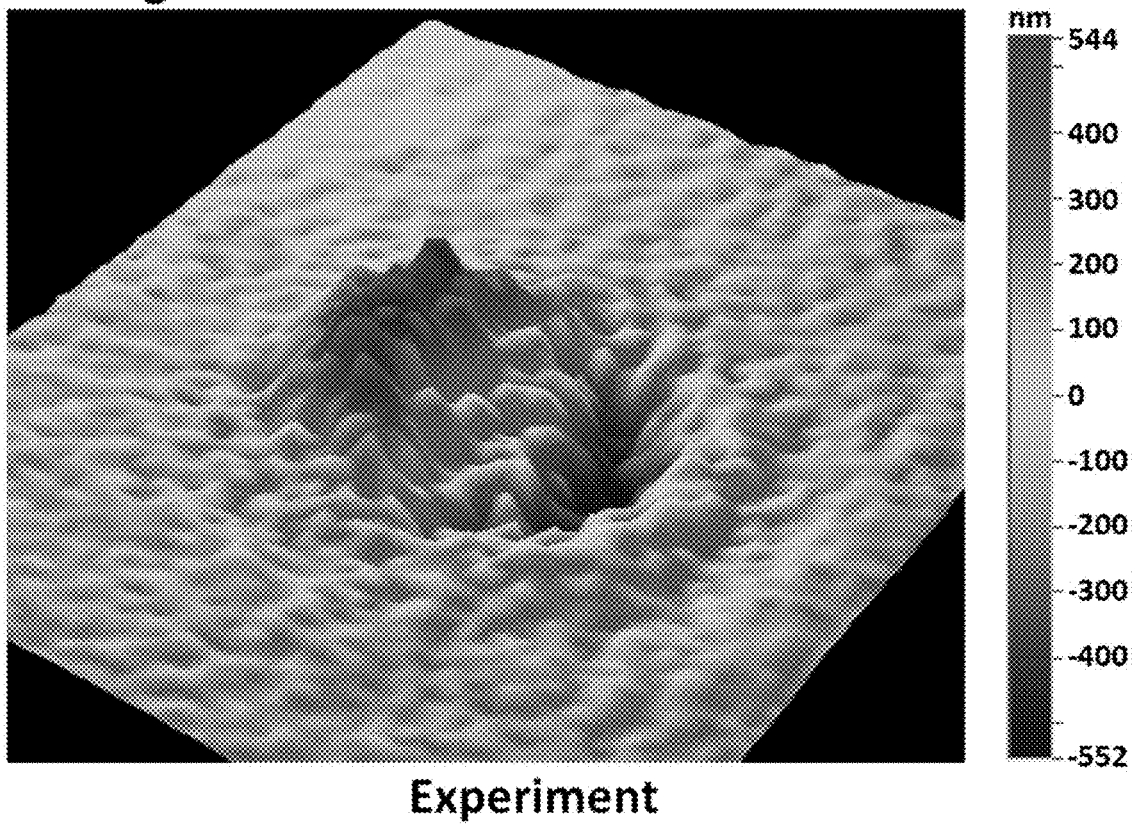
*Fig. 8, cont'd.*

SINGLE-PIXEL OPTICAL TECHNOLOGIES FOR INSTANTLY QUANTIFYING MULTICELLULAR RESPONSE PROFILES

CROSS-REFERENCE TO RELATED APPLICATIONS

This application is a U.S. 371 National Phase of PCT/US2018/040805, filed on Jul. 3, 2018, which claims benefit of and priority to U.S. Ser. No. 62/528,405, filed on Jul. 3, 2017, both of which are incorporated herein by reference in their entirety for all purposes.

STATEMENT OF GOVERNMENTAL SUPPORT

This invention was made with government support under Grant Number GM114188, awarded by the National Institutes of Health. The Government has certain rights in the invention.

BACKGROUND

In multicellular organisms, chemical gradients, electrical impulses, and force propagation transmit signals to elicit cell responses far from the signal origin. For example, at a macroscale, an electrical stimulus originating at the sinoatrial node at the base of the heart and moving rapidly to the apex of the heart is observable on an electrocardiogram and represents an electrical impulse propagating through millions of cells with a pattern that is interpretable as the functional condition of the heart. In another example, cells may be near or distal to the source of a chemical hormone signal and a measurable chemical gradient established by that hormone signal provides organizing information as illustrated, for example, by ecdysone in molting insects.

Despite these and numerous other examples of simple technologies that quantify electrical and chemical interactions between collections of cells that elicit larger scale biological activities, no technology currently exists to quantify rapid mechanical cell responses to transmitted distal perturbations for all cells within a collection of cells. In the bodies of various organisms (e.g., mammals), cells (other than blood cells) reside within interconnected two- and three-dimensional sheets and clusters. Yet current biophysical approaches quantify viscoelasticity (i.e., Young's modulus, E), for only one to a few cells at a time for typically sized metazoan cells.

Progress over the past several decades has provided tools and approaches for quantifying the mechanical properties of cells. Representative approaches include, for example, atomic force microscopy (AFM), which provides accurate cell deformation data with high spatial resolution measurements for single cells, but is slow and requires serial repositioning of the AFM tip to obtain statistically significant data that lacks mechanical contributions from nearby cells (Cross et al. (2007) *Nat. Nanotechnol.* 2: 780-783; Cross et al. (2009) *Nat. Nanotechnol.* 4: 72-73; Cross et al. (2008) *Nanotechnology,* 19: 384003; Reed et al. (2007) *Nanotechnology,* 18: 044032). Traction force microscopy (TFM) quantifies force exerted by and between cells within a sheet grown on top of an underlying gel substrate. Measurements of the deformation of the gel with known viscoelasticity by optical tracking of embedded nanoparticle movements provides the traction forces transmitted from overlying cells (Hammer et al. (2005) *Abstr Pap Am Chem S* 229, U648-U648; Holenstein et al. (2017) *Sci Rep-Uk* 7//doi.org/10.1038/srep41633; Jorge-Penas et al. (2015) *Comput. Meth. Biomec.* 18: 1377-1385; Morin et al. (2014) *Exp. Cell Res.,* 326(2): 280-294; Morin et al. (2014) *Exp. Cell Res.* 326: 280-294; Mulligan et al. (2017) *Biomed. Opt. Express,* 8: 1152-1171; Peschetola et al. (2013) *Cytoskeleton* 70: 201-214; Style et al. (2014) *Soft Matter* 10: 4047-4055; Tang et al. (2014) *Plos Comput. Biol.* 10: 10. e1003631; Toyjanova et al. (2015) *Biophys. J.* 108: 493A-493A; Vitale et al. (2012) *J. Math Anal. Appl.* 395: 788-801; Balaban et al. (2001) *Nat. Cell Biol.* 3: 466-472).

Elastic pillars (EP) are also useful for traction force measurements. In this approach, numerous independent pillars of known viscoelastic material underlie a sheet of adherent cells to provide a platform for easy extraction of cell forces by optically quantifying the deflections of multiple pillar tips (Tan et al. (2003) *Proc. Natl. Acad. Sci. USA,* 100: 1484-1489; du Roure et al. (2005) *Proc. Natl. Acad. Sci. USA,* 102: 2390-2395; Yang et al. (2007) *Adv. Mater.* 19: 3119-3123; Ricart et al. (2011) *Biophys. J.* 101: 2620-2628; Ghassemi et al. (2012) *Proc. Natl. Acad. Sci. USA,* 109: 5328-5333; van Hoorn et al. (2013) *Biophys. J.* 104: 193A-193A; Bashour et al. (2014) *Proc. Natl. Acad. Sci. USA,* 111: 2241-2246; Fu et al. (2010) *Nat. Meth.* 7: 733-736; Vedula et al. (2012) *Proc. Natl. Acad. Sci. USA,* 109: 12974-12979). Yet, both TFM and EP platforms require high magnification 60× or 100× objective lenses to accurately locate the positions of tracer particles or pillar tips, which significantly limits the field-of-view (FOV) and number of cells in a sheet that can be concurrently measured. Although it is possible to sequentially collect data across a larger area than ~3 typically-sized metazoan cells and piece the collected information together, these measurements are limited to slow cellular responses, and often cells are chemically treated in some manner to enable required long scan times, impairing dynamic real-time measurements. Thus, it remains impossible with current platforms or technologies to capture the fast, dynamic, and collective cellular mechanical responses typical for intercellular force communication in tissues that span multiple length scales.

Beating cardiomyocytes (CMs) that periodically contract, synchronize, and propagate mechanical forces through centimeter and longer length-scales provide one representative example that is currently inaccessible to large-scale force studies. Muscular thin film (MTF) technology provides collective cell contraction behavior by patterning cells on one side of a flexible polymer thin film that resembles a flexible cantilever (Reed et al. (2008) *ACS Nano,* 2: 841-846; Barer (1952) *Nature,* 169: 366-367; Ross, K. Phase Contrast and Interference Microscopy for Cell Biologists. (Edward Arnold, Ltd., 1967); Xiao et al. (2017) in *IEEE MicroElectroMechanical Systems (MEMS '17)* 243-246 (Las Vegas)). When cells contract, the imbalanced stress across the film causes the film to bend and its extent of bend provides an indicator for force generation efficiency. However, MTF only gives a single average displacement number for force of the collective cells contracting or relaxing and does not provide data for individual cells making up the collective and their potential synergistic, antagonistic, or additive force generating activities.

There are major fundamental limitations of current optical approaches, such as TFM and EP, and cantilever deflection based approaches, such as AFM and MTF, for scaling up measurements to interrogate force interactions between sheets/clusters of cells. For example, optical approaches typically require precise tracking of locations and displacements of tracer particles to provide quantitative force data, which necessitates a high numerical aperture (N.A.) objective lens and high magnification and significantly limits the field of view (FOV) to a few cells at most. Digital camera obtained nanoparticle images mathematically fitted to Gaussian curves track nanoparticle locations with accuracy below one optical pixel, but this one step in data interpretation requires many digital pixels to narrow the error between the "true" particle location and the predicted one. Using lower N.A. optics to capture larger measurement areas to interrogate force generation and propagation over sheets of cells introduces several negative factors that significantly reduce particle tracking accuracy and create faulty biomechanical values. First, fewer CCD pixels are available for imaging each nanoparticle since the same number of digital pixels covers more nanoparticles across a larger projected area. This affects mathematical curve fitting accuracy. Second, the object size that each digital pixel represents increases, meaning that the error between the "true" object location and the curve fitting predicted location also increases even when using the same number of pixels. Third, the captured optical signals from each nanoparticle weaken due to the small light collection angle of low N.A. optics, which lowers the signal-to-noise ratio and tracking accuracy. These fundamental optical limitations combine to make current particle tracking approaches impossible for large area quantitative data collection and attempts to overcome these physical limitations over the past decade have failed. A radical shift from current detection and measurement methods is required to overcome these technology hurdles.

SUMMARY

In various embodiments, new platform technologies to actuate and sense force propagation in real-time for large sheets of cells are provided. The multiplexed dual actuator and sensor technology provided herein overcomes current limitations in quantifying mechanical cell interactions spatially and temporally over large distances as occur in vivo for multicellular organisms. In this regard, FIG. 1 provides a comparison of current technologies for quantifying cell deformation and/or traction forces and the key gap in this spectrum of approaches that new Single-Pixel Optical Technologies (SPOTs) described herein overcome.

Various embodiments contemplated herein may include, but need not be limited to, one or more of the following:

Embodiment 1: A device for the measurement of mechanical properties of cells or other moieties, said device comprising:
  a transparent elastic or viscoelastic polymer substrate disposed on a rigid transparent surface; and
  a plurality of micromirrors disposed on or in said polymer substrate, wherein the reflective surfaces of said micromirrors are oriented substantially parallel to the surface of said polymer substrate.

Embodiment 2: The device of embodiment 1, wherein said micromirrors comprise a surface coated with a magnetic material.

Embodiment 3: The device of embodiment 2, wherein said micromirrors comprise a surface coated with a ferromagnetic material.

Embodiment 4: The device of embodiment 3, wherein said ferromagnetic material comprises a material selected from the group consisting of iron, nickel, cobalt, and alloys thereof.

Embodiment 5: The device of embodiment 3, wherein said ferromagnetic material comprises nickel.

Embodiment 6: The device according to any one of embodiments 1-5, wherein said micromirrors further comprise an optical diffraction grating.

Embodiment 7: The device of embodiment 6, wherein said micromirrors comprise 2-D grating structures.

Embodiment 8: The device according to any one of embodiments 6-7, wherein said diffraction grating(s) comprise from about 600, or from about 700, or from about 800 up to about 2000 grooves/mm, or from about 1,000 up to about 1600 grooves/mm, or from about 1100 up to about 1300 grooves/mm, or about 1200 grooves/mm.

Embodiment 9: The device of embodiment 8, wherein said diffraction grating comprises about 1200 grooves/mm.

Embodiment 10: The device according to any one of embodiments 1-5, wherein said polymer comprises PDMS.

Embodiment 11: The device according to any one of embodiments 1-10, wherein the thickness of said polymer is selected to effectively decouple tilting behaviors of neighboring mirrors.

Embodiment 12: The device according to any one of embodiments 1-11, wherein the Young's modulus (E) of the polymer is about the stiffness of a typical mammalian cell.

Embodiment 13: The device according to any one of embodiments 1-11, wherein the Young's modulus (E) of the polymer ranges from about 1 kPa to about 40 kPa.

Embodiment 14: The device according to any one of embodiments 1-13, wherein said rigid transparent surface comprises a glass surface.

Embodiment 15: The device according to any one of embodiments 1-14, wherein said device comprises at least 1,000 micromirrors, or at least 10,000 micromirrors, or at least 100,000 micromirrors, or at least 1,000,000 micromirrors, or at least 5,000,000 micromirrors, or at least 10,000,000 micromirrors.

Embodiment 16: The device according to any one of embodiments 1-15, wherein the distance between neighboring mirrors ranges from about 5 μm, or from about 10 μm, or from about 20 μm, or from about 30 μm, or from about 40 μm, or from about 50 μm up to about 200 μm, or up to about 150 μm, or up to about 100 μm.

Embodiment 17: The device according to any one of embodiments 1-16, wherein said micromirrors are present at a density of at least about 1 million micromirrors/25 cm$^2$, or at least about 5 million micromirrors/25 cm$^2$, or at least about 10 million micromirrors/25 cm$^2$.

Embodiment 18: The device according to any one of embodiments 1-17, wherein said micromirrors have a maximum dimension normal to the reflective face of less than about 50 μm, or less than about 40 μm, or less than about 30 um, or less than about 20 μm, or range in size from about 1 μm or from about 3 μm or from about 5 μm up to about 30 μm, or up to about 25 μm, or up to about 20 um, or up to about 10 μm.

Embodiment 19: The device of embodiment 18, wherein said micromirrors have a maximum dimension normal to the reflective face ranging from about 5 μm to about 20 μm.

Embodiment 20: The device of embodiment 18, wherein said micromirrors have a maximum dimension normal to the reflective face ranging from about 5 μm to about 20 μm.

Embodiment 21: The device of embodiment 18, wherein said micromirrors have a maximum dimension normal to the reflective face ranging from about 5 μm to about 10 μm.

Embodiment 22: The device according to any one of embodiments 1-21, wherein said micromirrors are circular, ovoid, square, rectangular, or an irregular polygon.

Embodiment 23: The device according to any one of embodiments 1-22, wherein said micromirrors have an aspect ratio ranging from about 1 up to about 20.

Embodiment 24: The device of embodiment 23, wherein said micromirrors have an aspect ratio of about 1.

Embodiment 25: The device of embodiment 24, wherein said micromirrors are substantially circular.

Embodiment 26: The device according to any one of embodiments 1-25, wherein the thickness of said micromirrors ranges from about 1 µm, or from about 5 µm, or from about 10 µm up to about 50 µm, or up to about 40 µm, or up to about 30 µm, or up to about 20 µm, or up to about 15 µm.

Embodiment 27: The device of embodiment 26, wherein the thickness of said micromirrors is about 10 µm.

Embodiment 28: The device according to any one of embodiments 1-27, wherein said micromirrors have an index of refraction at least twice the index of refraction of said polymer substrate.

Embodiment 29: The device according to any one of embodiments 1-28, wherein said micromirrors comprises a material selected from the group consisting of silicon, gallium arsenide, gallium phosphide, and germanium.

Embodiment 30: The device of embodiment 29, wherein said micromirrors comprise silicon.

Embodiment 31: The device according to any one of embodiments 1-30, wherein each of said micromirrors is a single crystal.

Embodiment 32: A system for quantifying mechanical interactions in multicellular biological systems, said system comprising:
 a device according to any one of embodiments 1-5, and 10-28, (e.g., wherein said mirrors do not comprises a diffraction grating); and
 a coherent light source that illuminates the reflective surface of said micromirrors.

Embodiment 33: The system of embodiment 32, wherein said coherent light source comprises a laser.

Embodiment 34: The system of embodiment 32, wherein said coherent light source comprises a light emitting diode (LED).

Embodiment 35: The system of embodiment 34, wherein said LED emits light at a wavelength of about 535 nm.

Embodiment 36: The system according to any one of embodiments 32-35, wherein said system further comprises an interferometer, an interference microscope, or a phase camera configured to detect phase changes of light reflecting from said micromirrors and measure changes in micromirror position.

Embodiment 37: The system according to any one of embodiments 32-36, wherein said system comprises an imaging device.

Embodiment 38: The system according to any one of embodiments 32-37, wherein said interferometer, an interference microscope, or a phase camera is configured to detect vertical displacement of said micromirrors.

Embodiment 39: The system according to any one of embodiments 37-38, wherein said system is configured to detect vertical displacement of said micromirrors using a single pixel.

Embodiment 40: The system according to any one of embodiments 37-39, wherein said system is configured to detect vertical displacement of less than 1 nm.

Embodiment 41: The system according to any one of embodiments 37-40, wherein said system is configured to detect tilting of said micromirrors.

Embodiment 42: The system of embodiment 41, wherein said tilting is detecting using two pixels in each tilt direction.

Embodiment 43: A system for quantifying mechanical interactions in multicellular biological systems, said system comprising:
 a device according to any one of embodiments 6-28, (e.g., wherein said mirrors comprise a diffraction grating); and
 a broadband light source that is collimated and illuminates the reflective surface and diffraction grating of said micromirrors.

Embodiment 44: The system of embodiment 43, wherein said micromirrors comprises a 2-D grating structure and said system uses two orthogonal broadband light sources.

Embodiment 45: The system according to any one of embodiments 43-44, wherein said system comprises a low N.A. lens with a small detection angle to pick up a narrow band of light reflected from said micromirrors.

Embodiment 46: The system according to any one of embodiments 43-45, wherein said system further comprise a CCD camera.

Embodiment 47: The system of embodiment 46, wherein CCD camera is disposed to detect a different and distinguishable color(s) as said micromirrors tilt.

Embodiment 48: The system according to any one of embodiments 43-47. wherein said system is configured to utilize a single pixel to detect tiling of a mirror.

Embodiment 49: A method of quantifying mechanical properties and/or interactions in multicellular biological systems, said method comprising:
 providing a plurality of cells on the surface the viscoelastic polymer in a system according to any one of embodiments 32-42; and
 using said interferometer, interference microscope, or a phase camera to detect phase changes of light reflecting from said micromirrors and to provide measures changes in micromirror position indicating the mechanical properties of cells comprising said system.

Embodiment 50: The method of embodiment 49, wherein said method comprises detecting vertical movement of said micromirrors.

Embodiment 51: The method of embodiment 50, wherein said vertical movement is detected using a single pixel.

Embodiment 52: The method according to any one of embodiments 49-51, wherein said method comprises detecting tilt of said micromirrors.

Embodiment 53: The method of embodiment 52, wherein tilt is detected using two pixels in each tilt direction.

Embodiment 54: The method according to any one of embodiments 49-53, wherein said method comprises applying a magnetic field to said micromirrors.

Embodiment 55: A method of quantifying mechanical properties and/or interactions in multicellular biological systems, said method comprising:
 providing a plurality of cells on the surface the viscoelastic polymer in a system according to any one of embodiments 43-48; and
 detecting the color of light reflected from said micromirrors to provide a measure of the orientation of said micromirrors and to provide measures changes in micromirror position indicating the mechanical properties of cells comprising said system.

Embodiment 56: The method of embodiment 55, wherein said method comprises detecting vertical movement of said micromirrors.

Embodiment 57: The method of embodiment 56, wherein said vertical movement is detected using a single pixel.

Embodiment 58: The method according to any one of embodiments 55-57, wherein said method comprises detecting tilt of said micromirrors by changes in the color of light reflected from said micromirrors.

Embodiment 59: The method of embodiment 52, wherein tilt is detected using a single pixel.

Embodiment 60: The method according to any one of embodiments 55-59, wherein said method comprises applying a magnetic field to said micromirrors.

Embodiment 61: The method according to any one of embodiments 49-60, wherein said method comprises determination of local and/or global cell contraction, and/or relaxation, and/or cell stiffness by determining the deformation of perturbed and non-perturbed system.

Embodiment 62: The method according to any one of embodiments 49-61, wherein said method comprises applying a magnetic force to micromirrors comprising said system and wherein vertical movement of said mirrors provides a measure of cell stiffness.

Embodiment 63: The method according to any one of embodiments 49-62, wherein tilting of said mirrors provides a measure of cell viscoelasticity, and/or deformability, and/or traction force, and/or angular and rotation force, and/or force propagation.

Embodiment 64: The method according to any one of embodiments 49-63, wherein said cells comprise clumps of cells.

Embodiment 65: The method according to any one of embodiments 49-63, wherein said cells comprise a confluent layer of cells.

Embodiment 66: The method according to any one of embodiments 49-63, wherein said cells comprise a monolayer of fibroblasts.

Embodiment 67: The method according to any one of embodiments 49-63, wherein said cells comprise a monolayer of cardiac myocytes.

Embodiment 68: The method according to any one of embodiments 49-63, wherein said cells comprise eukaryotic cells.

Embodiment 69: The method according to any one of embodiments 49-63, wherein said cells comprise mammalian cells.

Embodiment 70: The method according to any one of embodiments 49-63, wherein said cells comprise cells selected from the group consisting of fibroblasts, stem cells, cardiac myocytes, IPSCs, rescued cells containing transferred mitochondria.

Embodiment 71: The method according to any one of embodiments 49-70, wherein said method comprises contacting said cells with one or more test agents to determine the effect of said test agents on the mechanical properties and/or interactions in multicellular biological systems.

Embodiment 72: The method of embodiment 71, wherein said test agent comprises a pharmaceutical, a nucleic acid, an siRNA, a CRISPR construct, an antibody, and a small organic molecule.

Embodiment 73: The method of embodiment 71, wherein said test agent comprises an agent selected from the group consisting of a cardiotoxin, a cardiac stimulant, a cardiac suppressant, and an anti-cancer agent.

Embodiment 74: The method according to any one of embodiments 49-70, wherein said method comprises applying an external mechanical force to cells disposed in said system.

Embodiment 75: The method of embodiment 74, wherein said method comprises applying perpendicular force at one edge of the P-SPOTs platform with quantification of local and transmitted mechanical force.

Embodiment 76: The method according to any one of embodiments 74-75, wherein said method comprises activation of angular, lateral and rotational force at one edge of C-SPOTs platform with quantification of local and transmitted mechanical force.

Embodiment 77: The method according to any one of embodiments 74-76, wherein said method comprises patterned activation of perpendicular and/or lateral forces at specific locations or in timed sequences (e.g. an applied force gradient) within P-SPOTs and C-SPOTs platforms with quantification of local and transmitted mechanical force.

Embodiment 78: The method according to any one of embodiments 74-77, wherein said method comprises combined P-SPOTs and C-SPOTs actuation to evaluate combined effects of perpendicular and lateral forces with quantification of local and transmitted mechanical force.

Embodiment 79: The method according to any one of embodiments 74-78, wherein said method comprises determining $Ca^{2+}$ flux for cardiomyocyte monolayers.

BRIEF DESCRIPTION OF THE DRAWINGS

FIG. 4, panel B, shows SEM images showing the rigid and flat SCS mirrors before released from a SOI wafer and transferred into a soft PDMS.

FIG. 5, panel B, shows that when a 100 jmn spherical polystyrene bead is pressed onto the P-SPOTs surface, the local deformation of the elastomer substrate is easily detected and quantified by the tilting and displacement through a 20× objective lens on the LCI interferometer.

FIG. 8, panel B, shows an optical QPM measurement showing a nickel disk (5 μm in diameter and 0.5 pm in thickness) causing a tilt similar to that caused by traction force under the actuation of an external magnetic field.

DETAILED DESCRIPTION

Figure 1:
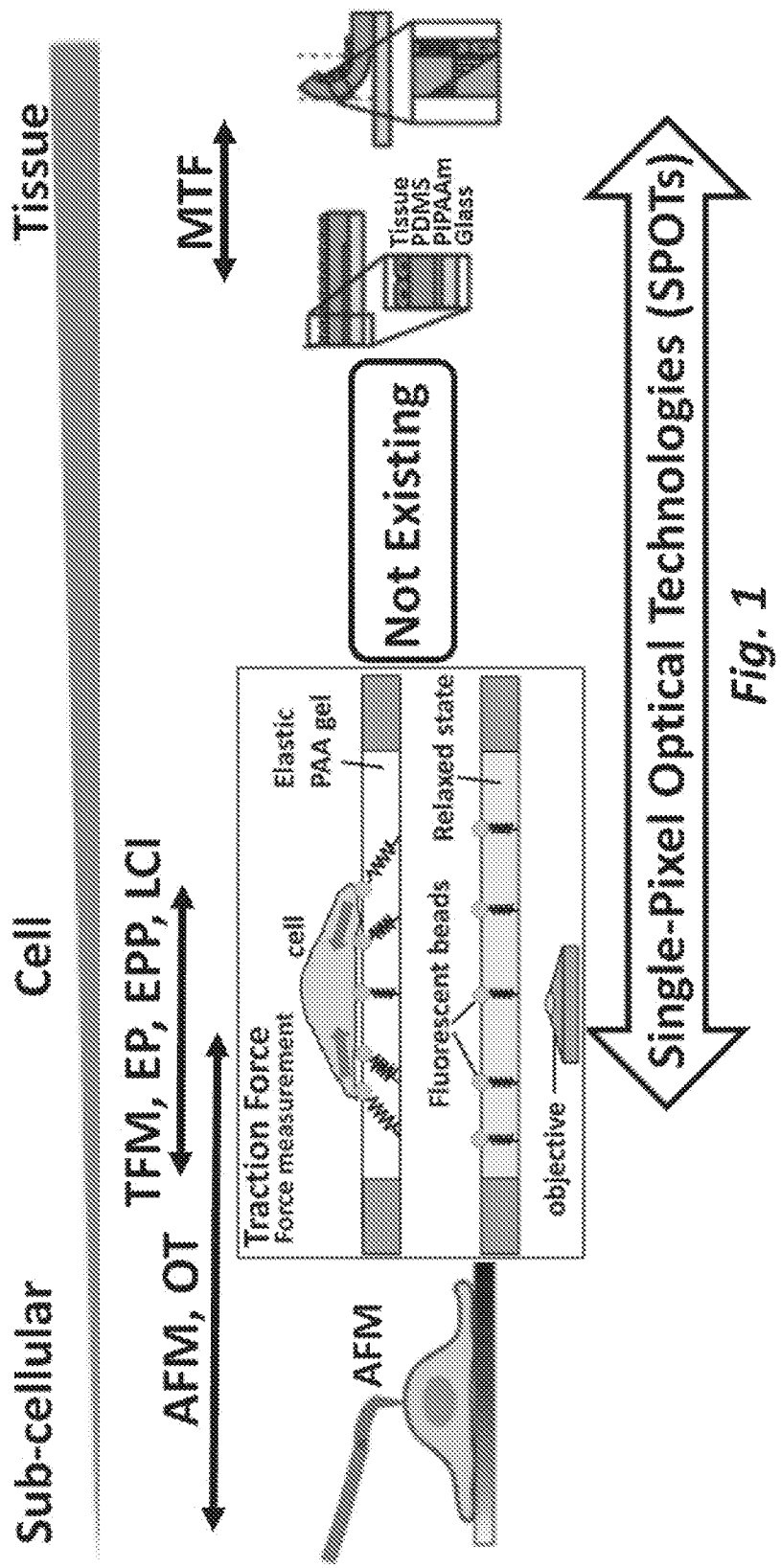
FIG. 1 illustrates a comparison of current technologies for quantifying cell mechanical properties. Current approaches obtain viscoelastic or generated traction force data on the sub-cellular, single cell, or several cells at a time scale. Example tools include atomic force microscopy (AFM), optical tweezers (OT), traction force microscopy (TFM), and elastic pillars (EP). Other approaches include, but are not limited to elastic plasmonic pillars (EPP) (see, e.g., PCT/US2016/042327) and live cell interferometer (LCI) approaches (see, e.g., U.S. Patent Pub. Nos: 2014/0178865 and 2016/0103118). However, it is believed that no previous technology can quantify rapid force propagation between cells, changes in cell deformability, or the simultaneous collective mechanical cell interaction forces over large distances and cell numbers. Muscular thin film (MTF) quantifies the average assembled traction force exerted by a group of cells and lacks individual cell contributions. The SPOTs platforms described herein are believed to fill a major technology gap and provide the first enabling approach for large-scale multimodality force actuation and sensing with sub-cellular spatial resolution.

As described herein in various embodiments, holistic, real-time actuation/detection systems for multicellular biomechanics are provided. The systems described herein enable fundamental biological investigations and provide new tools to quantify the quality of futuristic, advanced cellular therapeutics that heretofore have been impossible to ascertain. The ultrahigh sensitivity optical phase mechanical platforms described herein enable, for the first time, concurrent and dynamic measurements of multiple cellular mechanical properties (viscoelasticity and deformability, traction force, angular and rotation force, force propagation, and others) across a large multicellular area. This new approach and platform technology is attractive for studying fast collective cellular behaviors and obtaining critical data, such as how high (or low) quality stem cell-derived cardiomyocytes compare to natural cardiomyocytes in their ability to generate force over large distances and to coordinate mechanical signals for synchronized beating.

Current approaches for quantifying cell stiffness/deformability and traction forces cannot capture rapid and dynamic changes in cellular biomechanical properties that propagate or transmit between numerous cells over long distances. Accordingly the platform technologies described herein (Phase-SPOTs (P-SPOTs) and Color-SPOTs (C-SPOTs)) were developed to overcome these problems. Both P-SPOT and C-SPOTs utilize immense arrays of high quality micromirrors embedded near the surface of a soft polymer substrate of adjustable stiffness/deformability. In certain embodiments the micromirrors are magnetically responsive. SPOTs detection relies on reflected optical signals, with those scattered in the direction perpendicular to the substrate surface providing quantitative data for changes in local sub-cellular deformability and motion, and with induced tilt of each mirror using, in certain embodiments, only one single optical pixel on a digital camera providing quantitative data on force propagation.

In various embodiments the size (e.g., maximum dimension) of each precision micromirror is less than about 50 μm, or less than about 30 μm, or ranges in size from about 1 um or from about 3 um or from about 5 um up to about 30 um or up to about 20 um, or up to about 10 μm. In certain embodiments the micromirrors range from about 5 μm up to about 20 μm, or from about 5 μm up to about 10 μm, which is about the size of a resting mammalian lymphocyte and far less than the projected area of a typical adherent mammalian cell in interphase. Since these mirrors are flat and remain rigid during magnetic actuation, and their relative locations are fixed using modern microfabrication, together with mirror tilting and movement data, we can precisely quantify surface wrinkle patterns on the known polymer substrate at every embedded mirror to measure local changes of dynamic mechanical properties in real-time.

Of note, both P-SPOTs and C-SPOTs are completely compatible with low N.A. optics for large projected area detection since there are no optical signals of high spatial frequencies needed to determine their shape and locations, which were established during platform microfabrication. Furthermore, the flat and large optical area of each mirror ensures sufficient optical signal collection for high signal-to-noise ratios in all measurements.

Phase-SPOTs (P-SPOTs):

P-SPOTs utilize an exceptionally uniform and flat single crystalline silicon (or other material) surface as a reflection mirror for high sensitivity mapping of phase shifts in local optical path length induced in polymer substrates of controllable viscoelasticity. Optical path length phase shifts arise from forces provided by the overlying cells and/or with magnetic actuation of each individual mirror or set of mirrors (e.g., patterns and gradients) perpendicular, angulated, or twisted relative to the cell sheet surface. Detection of vertical movement of each individual mirror requires only one single CCD pixel to extract precise optical phase shifts for each mirror, for millions of mirrors simultaneously over the large FOV. Phase shifts provide sub-nanometer resolution of vertical displacement to relay precise cell motion and stiffness data at each mirror, as shown for LCI technology in U.S. Patent Pub. Nos: 2014/0178865 and 2016/0103118 which are incorporated herein by reference for the live cell interferometry (LCI) methods and devices described therein.

Figure 2:
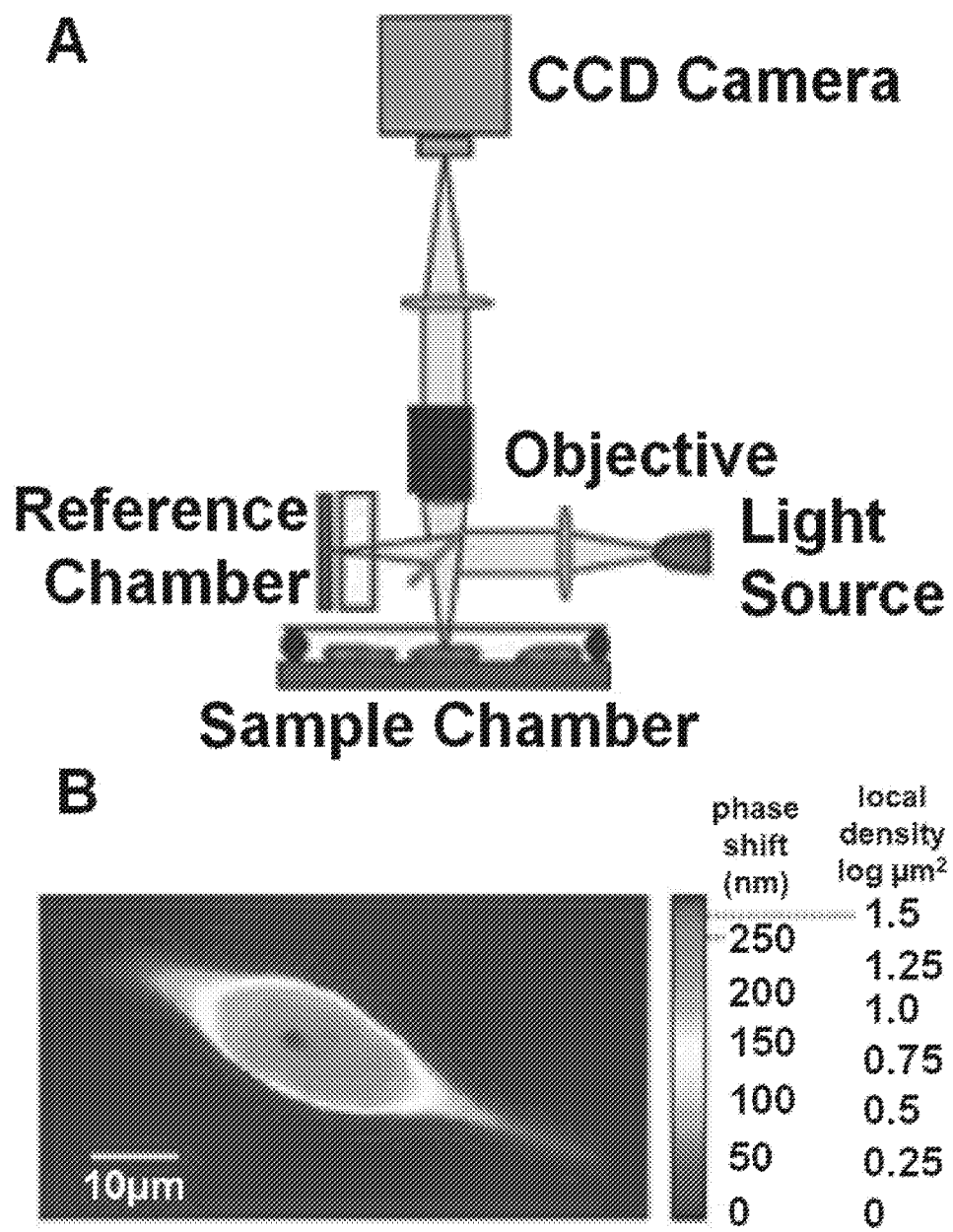
FIG. 2, panels A-B, illustrate live cell interferometry (LCI). Panel a) LCI, as illustrated, utilizes a microscope that compares the "optical thickness" of fluid in a reference chamber to the "optical thickness" of cells in a sample chamber. In certain embodiments cells are kept at pH 7.4, 37° C., 5% $CO_2$. Panel b) LCI image of a live fibroblast with color coding for local density. Summing local densities across the cell area multiplied by a conversion factor, α, provides biomass of a cell. Changes in biomass can be determined as differences in summed biomass over time.

Precision Single-Cell Response Profiling with a Live Cell Interferometer (LCI):

Real-time biomass profiling of cells is a new and reproducible method for quantifying single cell growth and growth rates using principles of quantitative phase shift microscopy (QPM). Optical methods or micro-fabricated sensors provide rapid quantification of single-cell biomass changes, or more relevant to this proposal, for changes in biomass distribution, cell motion, and cell deformability for a population of cells over time, such as during cell differentiation (Burg et al. (2007) *Nature,* 446: 1066-1069; Godin et al. (2010) *Nat. Meth.* 7: 387-390; Popescu et al. (2008) *Am. J. Physiol. Cell Physiol.* 295: C538-544; Reed et al. (2011) *Biophys. J.* 101: 1025-1031; Zangle & Teitell (2014) *Nat. Meth.* 11: 1221-1228). Multi-PI Teitell co-invented the LCI and have shown reproducible picogram sensitivity (Reed et al. (2008) *Nanotechnology* 19: 235101; Reed et al. (2008) *ACS Nano,* 2: 841-846) (FIG. 2). The LCI principal is as follows: the variation in phase imparted to coherent light propagating through a transparent cell body is linearly proportional to its density (Barer (1952) *Nature,* 169: 366-367; Ross, K. Phase Contrast and Interference Microscopy for Cell Biologists. (Edward Arnold, Ltd., 1967)). Interference patterns quantify changes in light phase to a precision <1/1000 of a wavelength, or better than 0.5 nm for visible light. Cell biomass (and rates of biomass redistribution and by conversion cell deformability) is related to light phase shifts for each cell as:

$$m = \frac{1}{\alpha} \int \phi \lambda \, dA$$

where m is the biomass of a cell, $\alpha$ is a constant that relates phase shift to cell biomass, $\phi$ is the measured fractional phase shift, $\lambda$, is the illumination wavelength, and integration is performed across the cell area, A. For mammalian cells and cancers, $\alpha=1.8\times10^3$ $m^3kg^1$, consistent with Ross (Ross, K. Phase Contrast and Interference Microscopy for Cell Biologists. (Edward Arnold, Ltd., 1967)) as an average value for cell contents like nucleic acids, proteins, lipids, and sugars. The LCI principle of QPM reflections is the basis for detection of micro-mirror vertical and angular displacements using P-SPOTs technologies.

P SPOTS Working Principle.

Figure 3:
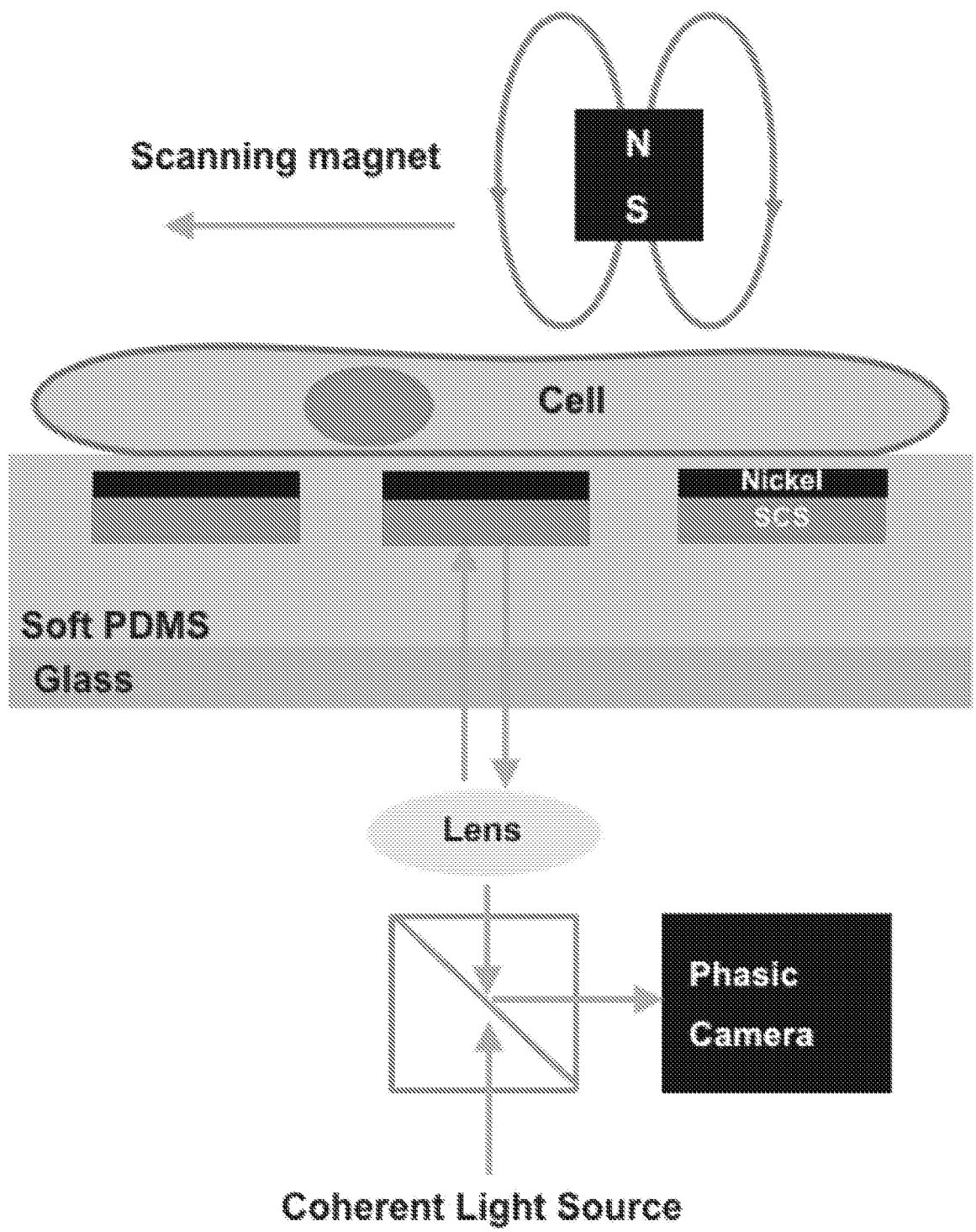
FIG. 3 illustrates the working principle of P-SPOTs. Detection of the movements of embedded silicon micromirrors is by a QPM (quantitative phase microscopy) optical phase camera, as for LCI. Active external magnetic mirror force actuation can be local, patterned, or temporal by scanning a magnet across the chip.

FIG. 3 illustrates the working principle of P-SPOTs. Our approach takes advantage of ultra-high sensitivity optical phase shift measurements, which we pioneered for live cells during LCI studies described (see, e.g., U.S. Patent Pub. Nos: 2014/0178865 and 2016/0103118). We couple LCI reflective QPM principles with an optically transparent tunable elastic substrate platform containing millions of embedded high performance micro-mirrors. A coherent light source, e.g., green diode (e.g., center frequency 535 nm), illuminates the mirrors, with light reflected and imaged by an interferometer though a lens using the same physical principle as the LCI. In principle, interference discriminates the distance and changes in distance of mirrors below 1 nm resolution, which can be directly related to changes in force instantaneously by knowledge of the viscoelastic/deformability properties of the platform. The lateral FOV resolution is set by the N.A. of the objective lens; but in P-SPOTs operation, lateral resolution is less important, unless details of cell features require simultaneous interrogation. In this event, in certain embodiments, a separate optical pathway can be constructed on the opposite side of the P-SPOTs elastic platform substrate.

With applied mechanical forces on a P-SPOTs platform, either from cells or by other external sources such as micro-mirror magnetic actuation, a PDMS elastomer deforms to cause micro-mirror titling and/or position translation that is quantified. Decoupling of the mechanical deformation caused on each mirror is by experimental control of mirror spacing and the viscoelasticity and the thickness of the PDMS layer between mirrors and a bottom hard glass substrate. Extraction of local and global cell contraction, relaxation and cell stiffness data is by analyzing the perturbed and non-perturbed P-SPOTs platform deformation.

P-SPOTs Fabrication.

Figure 4:
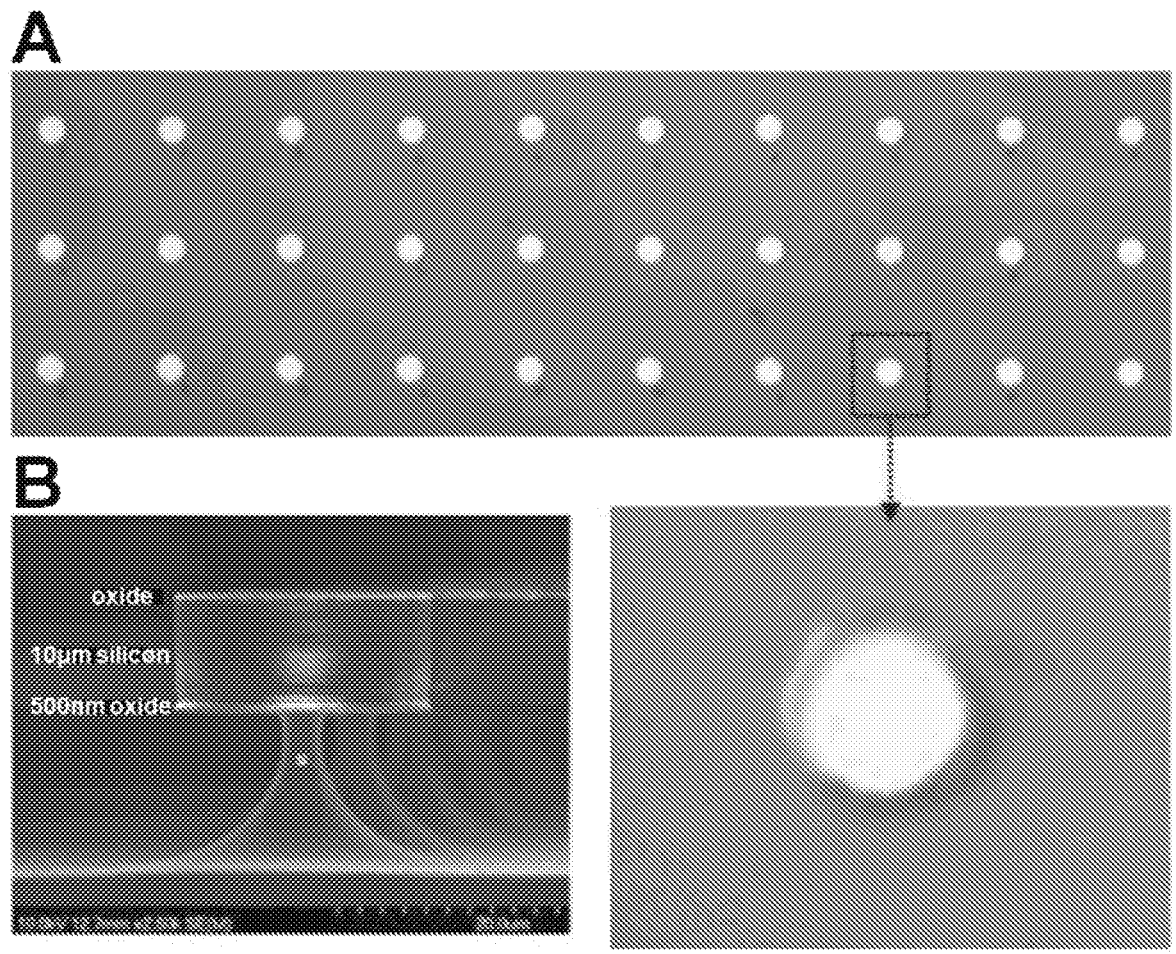
FIG. 4, panel A, optical images of single crystalline silicon (SCS) mirrors embedded in PDMS.

In certain embodiments fabrication of the P-SPOTs heterogeneously integrated device platform is by hybrid stamp soft lithography and transfer approaches developed in Contact-Pl's lab for the integration of high-aspect-ratio single crystalline silicon (SCS) and soft polymer structures (Liu, T., Wen, X., Kung, Y.-C. & Chiou, P. Y. in IEEE Micro Electro Mechanical Systems (MEMS '17) 663-666 (Las Vegas; 2017); Kung et al. (2015) *Lab Chip,* 15: 1861-1868; Kung et al. (2016) *Small,* 12: 4343-4348). FIG. 4 shows actual optical images of a micro-fabricated P-SPOTs testing platform. The platform has several innovative and critical enabling features. First, the embedded SCS mirrors are generated, released, and transferred from the device layer of a commercially available silicon-on-Insulator (SOI) wafer. In the illustrated embodiment, the mirror is 10 pm thick and 20 μm in diameter (FIG. 4). The thickness and the diameter of mirrors can be adjusted for different applications. Wafer-level polishing ensures the interface between silicon and thermal oxide layers (oxide layer is used as a sacrificial layer and not shown in the final fabricated structure) have atomic-level smoothness<1 nm, which provides a high quality reflecting mirror for optical phase QPM measurements. The high refractive index contrast between silicon (n=3.5) and PDMS (n=1.4) can provide high reflectance without an extra coating on the mirror. Other high refractive index materials (e.g., gallium arsenide, gallium phosphide, germanium, etc.) can be used. The illustrated rigid bulk silicon mirror (E=170 GPa) has a Young's modulus 6 orders of magnitude higher than typical mammalian cells (~10 kPa) and the surrounding soft PDMS elastomer (vary from 5-200 kPa) platform to guarantee extreme flatness under forces from either cells or magnets during optical phase measurements. A magnetic (e.g., nickel) layer is (or may not be) electroplated on the mirrors (e.g., silicon disks) before transfer for magnetic actuation.

P-SPOT Measurements of Local Cell Stiffness:

In one illustrative, but non-limiting, embodiment, to quantify local cell stiffness, a magnet bar can scan across the P-SPOTs platform (FIG. 3). A magnetic field from this bar is not uniform, the mirrors with nickel will sense it in real-time and be titled and translated in different ways, depending on their relative locations to the magnetic bar. The dynamic mirror movements can be recorded in real-time by QPM. With known magnetic field strength and distribution, and viscoelastic properties of soft PDMS, detected mirror tilting and translation can provide local cellular stiffness data.

Figure 5:
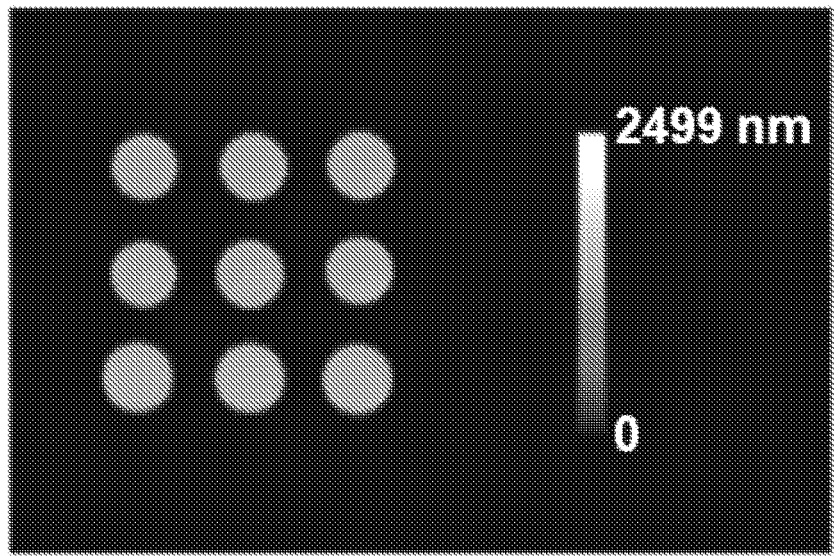
FIG. 5, panel A, shows optical phase measurement of embedded SCS mirrors before external force application.
Figure 5:
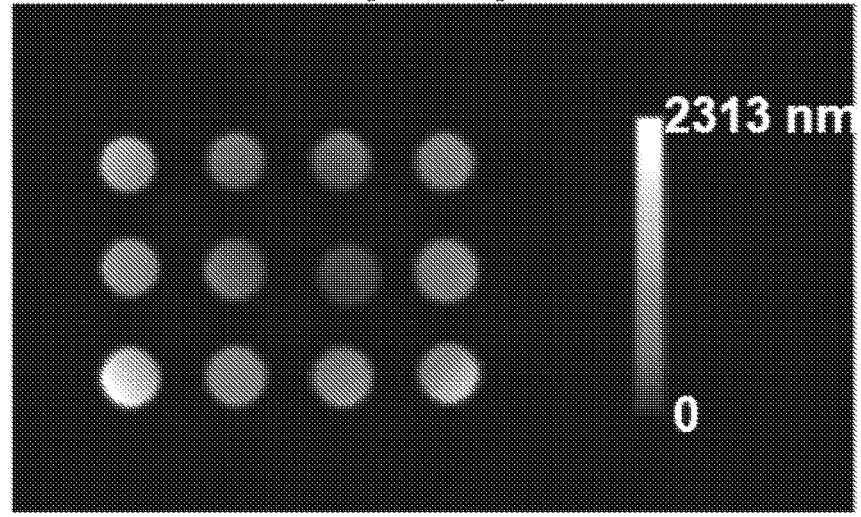

FIG. 5 shows mirror displacements without force application captured by the LCI interferometer through a 20× objective lens. Uniform displacement data confirms that the mirrors are extremely flat and even height in the PDMS elastomer substrate, and their locations are precision controlled. FIG. 5 also shows that when a spherical micro-bead deforms the P-SPOTs substrate, titling and vertical displacement data from different mirrors are easily captured. Every tilted micro-mirror shows only one linear slope through the entire mirror surface, confirming that all mirrors remain rigid and flat even when the surrounding PDMS structure is severely deformed by pressing.

Single Pixel Measurements, Spatial Resolution, and Field-of-View.

Our preliminary data in FIG. 5 is captured by a 20× objective lens. This means that >1,000 digital pixels are imaging a single mirror, which is undesirable. Extraction of the vertical displacement of a mirror requires only one single CCD pixel, with all other pixels redundant since the mirror is extremely flat. This means P-SPOTs force studies can use much lower N.A. optics as long as the reflected optical signal from a mirror is captured by at least one digital pixel and signals from neighboring mirrors do not interfere. Using a 10 mega-pixel phase camera with a 15 μm pixel size coupled to 1× imaging optics using a N.A. 0.04 lens, the optical diffraction limited spot size is 15 µm and the pitch distance between mirrors is also 15 µm (Goodman, J. W. Introduction to Fourier Optics. (McGraw-Hill, 1996)). With this example P-SPOTs system configuration, 10 million mirrors in a 5×5 cm² area can be interrogated in real-time over time to quantify local stiffness changes in millions of interconnected cells with a 15 µm spatial resolution. Furthermore, P-SPOTs can operate with a phase camera coupled with a zoom-in lens, so in fact there is no requirement for microscopy at all when there is no need to visualize cellular details or patterns. This allows adaptation of the P-SPOTs approach by other research labs for broader applications and impact. Depending on specific applications, the lens, camera, mirror size, and pitch are all adjustable for higher spatial resolution, even larger areas, or other system needs.

Results and Interpretations.

In certain embodiments, to measure static and changes in cell stiffness, the Young's modulus, E, of the polymer comprising the platform (e.g., PDMS) is tuned near typical mammalian cells' E (vary from 1-40 kPa) (Cross et al. (2007) *Nat. Nanotechnol.* 2: 780-783; Cross et al. (2009) *Nat. Nanotechnol.* 4: 72-73; Cross et al. (2008) *Nanotechnology*, 19: 384003; Haga et al. (2000) *Ultramicroscopy*, 82: 253-258; Xu et al. (2012) *Plos One*, 7(10): e46609; Qiu et al. (2010) *Circ. Res.* 107: 615-U117; Engler et al. (2004) *J. Cell Biol.* 166: 877-887). Then cell studies can inform variations in custom stiffness and mirror configurations. The P-SPOTs surface is flat with a continuous polymer (e.g., PDMS) layer that allows users to customize surface treatments, such as coating fibronectin or collagen for specific cell types, to promote cell adhesion, or other applications, for further examination.

As shown in FIG. 5, detection of mirror titling typically utilizes more than one single optical pixel to reflect the tilting slope of a mirror. A minimum of 2 pixels is typically in each direction to provide the vertical displacement at two different points to determine the linear slope. This will sacrifice the number of detection mirrors that can be simultaneously queried. A different SPOTs method called C-SPOTs (described below) provides an alternative strategy for quantifying single-pixel images that measure mirror tilting.

Color-SPOTs (C-SPOTs):

The P-SPOTs method typically utilizes multiple optical pixels to quantify mirror tilting, a key measure of applied and propagated force in multicellular sheets. This is not ideal for measuring traction forces from cells that are mainly tangential and parallel to the substrate surface, which causes the tilting movement of embedded mirrors. To realize single pixel measurements of mirror tilting, the Color-SPOTs (C-SPOTs) method was developed for single-pixel detection of, inter alia, traction force, cell stiffness, and to provide a different direction for actuation of mechanical force.

P-SPOTs can detect changes in mirror tilting with exerted or applied forces, but this comes at a price of requiring at least two CCD pixels to determine the tilting angle of each axis and leads down the slippery slope of current technology limitations. To determine mirror tilt using P-SPOTs also typically utilizes an optical interferometer or special phase camera for precision phase detection, which takes this technological innovation to a new level of complexity beyond the reach of many biology and even some engineering laboratories.

C-SPOTs provides a simplifying solution to these problems. C-SPOTs is a refined version of the flat P-SPOTs mirrors that integrates optical gratings on the polymer-embedded mirrors. Through properly controlled and adjusted grating periods, illumination angles, and incident light wavelengths, mirrors with different tilted angles reflect different compositions of colors in the light spectrum onto the imaging lens of a color-sensitive digital camera. Dynamic changes in the mechanical properties of cells encompassing a few centimeter-sized sheet can be quantified in real-time by color videography captured by a standard color digital camera coupled with a low cost 1× or 2× magnification lens. Furthermore, optical diffraction patterns can be two-dimensional with multi-axis tilting information obtained by the same optical pixel through sequential illumination of light beams from two orthogonal directions, providing rapid and simultaneous force data in orthogonal directions for all cells interrogated in a sheet.

Working Principle

Figure 6:
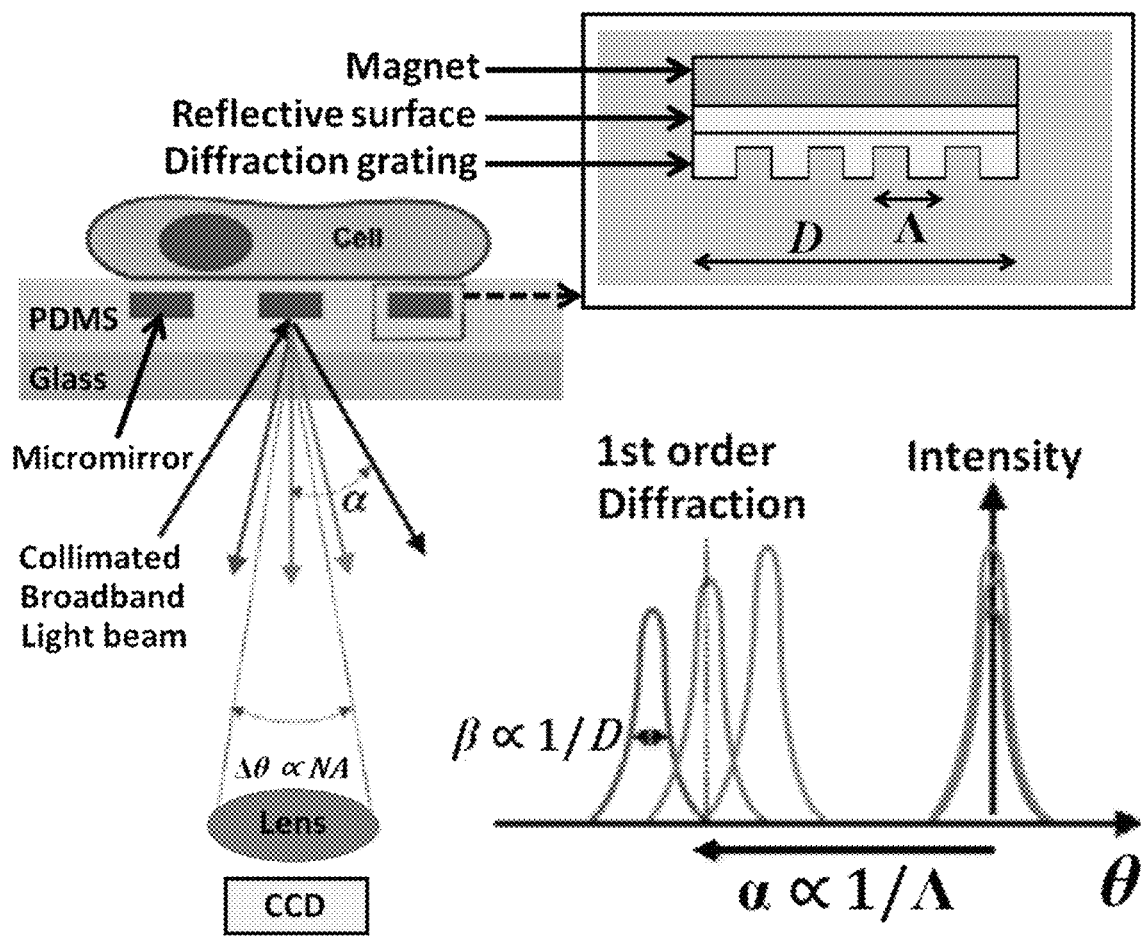
FIG. 6 illustrates the C-SPOTs operating principle that utilizes SCS mirrors with optical gratings. A collimated broadband light source illuminates a C-SPOTs mirror at a desired angle determined by grating periodicity (Λ). The grating causes color dispersion and reflects light beams of different colors in different directions. A low N.A. lens with a small collection angle (Δθ) picks up a narrow band of light from each mirror to image onto a CCD camera. The color detected from each mirror quantifies its amount of tilting. Mirror diameter (D) determines how sharp each color band is and will affect color sensitivity.

FIG. 6 illustrates the working principle of C-SPOTs. On the surface of high performance reflective mirrors (e.g., silicon mirrors), optical gratings are fabricated. When a collimated broadband light beam illuminates a mirror, the grating structure causes color dispersion and fractionated light beams of different colors reflect in different directions. Using a low N.A. lens to collect these reflective color beams, only light beams within a small reflection angle, or color band, are collected and imaged onto a CCD camera. When a grating mirror tilts due to applied force, either from cells or from magnetic actuation, it reflects a different color band into the low N.A. lens and causes a color change in the corresponding pixel on a color camera. By monitoring the color change of the corresponding pixel, calculate the tilt angle of the embedded mirror in the elastomer PDMS substrate and local applied force felt by the mirror can be calculated. Spatial resolution and FOV is the same as the P-SPOTs method. Local cell traction forces applied on grating mirrors and local cell stiffness data can be determined by measuring the dynamic tilting behavior of each mirror.

In addition, since diffraction optics are directional, two-axis tilting and in-plane rotation of embedded mirrors are also detected by fabricating 2-D grating structures and using two orthogonal broadband light beams. The operation of C-SPOTs requires only a typical color CCD camera, a simple 1 to 5× lens, and simple multicolor LEDs with collimation optics. These system requirements enable C-SPOTs to be used in numerous academic and commercial labs without purchasing expensive equipment or the need for highly specialized training once the basic features are established and understood. In fact, these color changes will be clearly observed with bare human eye that has a NA value of 0.01 (10 cm focal length and 1 mm pupil radius) for initial qualitative assessment of traction force amplitudes and propagation patterns on a C-SPOT platform.

The fabrication of C-SPOTs platforms is similar to P-SPOTs, except for one extra patterning process to create optical gratings on mirror surfaces before transfer from a SOI wafer. For a reference, a grating period ($\lambda$) of 2 µm on a mirror will result in a 15-degree bend of a green light beam (500 nm wavelength), a 28.6-degree bend of a blue light beam (450 nm), and 32.8-degree bend of a red light beam (600 nm) (Goodman, J. W. Introduction to Fourier Optics. (McGraw-Hill, 1996)). Mirror diameter determines the spreading angle ($\beta$) of each color. For a mirror 10 µm in diameter, $\beta$ is 2.8-degrees for all three colors. Using low N.A. optics with a collection angle ($\theta$), only a small color band dispersed by the mirror grating will be collected and imaged onto a pixel of a CCD camera. Low N.A. optics is better than a high N.A. optics for C-SPOTs operation since this configuration catches a narrow band of color and has higher color change sensitivity.

Figure 7:
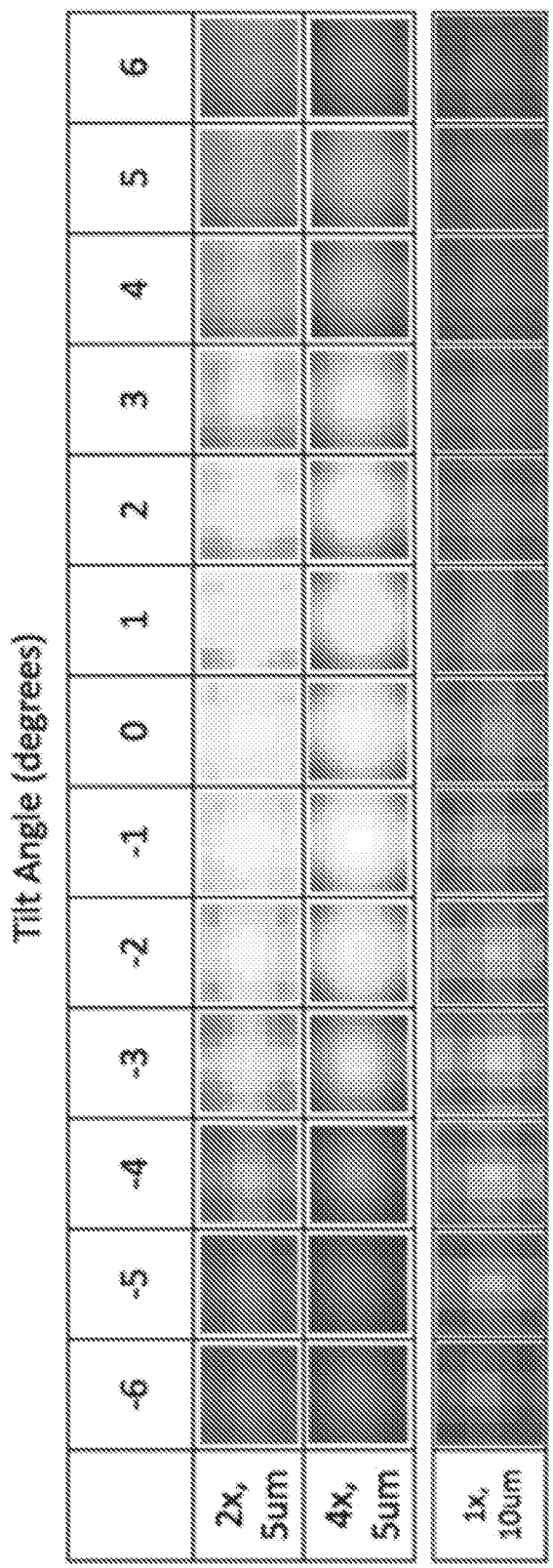
FIG. 7 shows preliminary data showing a 5 μm circular-shaped grating reflects different colors into 2× and 4× lenses detected by a typical single lens digital camera. The 1× and 2× lenses provide better color change sensitivity than the 4× lens as predicted by diffraction optics principles. Any pixel from a disk can be used to track and quantify the tilting angle of a grating mirror, which provides immediate and massively parallel data on forces felt by numerous interconnected cells.

FIG. 7 shows optical images of a 5 μm circular grating pattern with a grating period A of 1.38 μm (720 grooves/mm) captured by a digital camera with 2× and 5× lenses, and a 10 μm grating pattern imaged by a 1× lens for comparison. Clear color changes occur by tilting the grating patterns between −6 to +6 degrees in all cases. The 1× data shows the highest color change sensitivity, as predicted, since the large disk size causes a sharper color band and the N.A. is lower to collect only light within a smaller angle (a smaller color band). Any single pixel in a disk image reflects the amount of tilting of that disk. There is no need for multiple pixels.

Quantifying Cell Traction Forces

Figure 8:
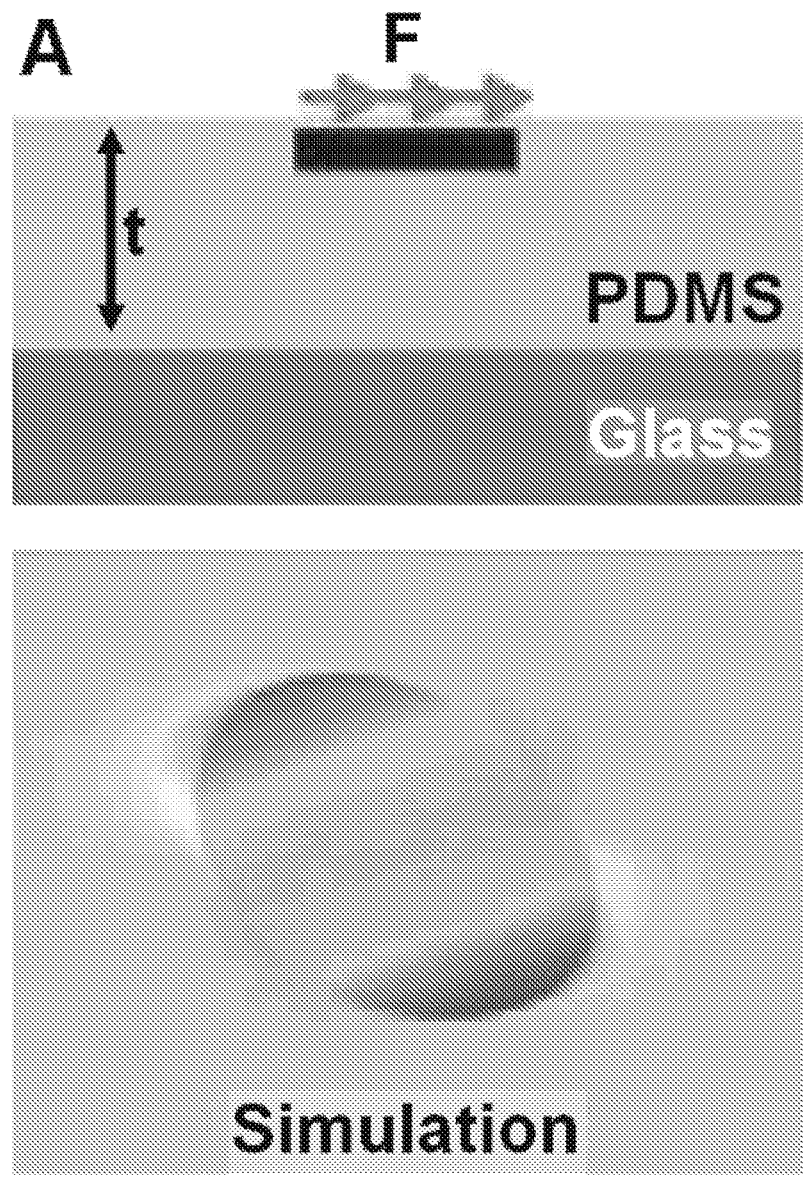
FIG. 8, panel A, shows a numeric simulation showing a tangential traction force applied on an embedded mirror causes tilting and local PDMS deformation.

The C-SPOTs platform provides a flat and continuous soft polymer (e.g., PDMS) that can be treated as desired to seed and grow cell sheets for studies. Forces generated by growing cells are mainly tangential since they organize in an interconnected sheet without counter acting forces on the other face of the cells. The cell traction force measured by a tilted mirror is the total sum of tangential forces applied at a region above each mirror. A thin PDMS layer coated on top of a mirror and the mirror's rigid nature ensure all forces applied on the surface transmit through to the mirror and sum as a single element to deform the surrounding PDMS elastomer. Cell traction forces applied outside a mirror will not significantly perturb each mirror's tilt unless very close to the edge of a mirror. Furthermore, tilting behaviors of neighboring mirrors decouple despite being on a continuous and connected film. This is because the force perturbation distance of a single mirror can be controlled by the PDMS thickness (t) between a mirror and the bottom rigid glass substrate to limit deformation to individual disks. (FIG. 8). Our design significantly simplifies the complexity of extracting forces in a continuous film.

FIG. 8, panel A simulates mirror tilting induced by applying a total 100 nN force on a 5 pm disk. For reference, common traction forces measured in prior works show a traction force density in the order of few nN/pm (Cross et al. (2009) *Nat. Nanotechnol.* 4: 72-73; Kajzar et al. (2008) *Biophys. J.* 94: 1854-1866; du Roure et al. (2005) *Proc. Natl. Acad. Sci. USA*, 102(7): 2390-2395).

FIG. 8, panel B shows the experimental data of a 0.5 μm thick, 5 μm sized magnetic nickel disk actuated by an external magnet providing a 0.01 Tesla magnetic field strength. Actuation results in a 10 degree tilt in a PDMS film (E=130 kPa). This simulation and actual data show that the effective force perturbation range from a mirror only extends by 2-3 μm from disk edges, which means when neighboring mirrors are separated by a distance>5 μm, there will be negligible deformation coupling. This effective perturbation range also applies to point forces applied by cells outside the mirror region as these forces will not affect mirror tilting and total traction force measurements by mirrors outside the perturbation range.

Quantifying Cell Stiffness by C-SPOTs.

Cell stiffness can be quantified by C-SPOTs using a principle similar to the method discussed above with respect to P-SPOTs. A magnetic bar will scan across (or located above) the C-SPOTs platform to induce dynamic tilting of mirrors. By quantifying the amount of tilting induced on each mirror, local stiffness will be calculated. The difference between P-SPOTs and C-SPOTs is that C-SPOTs uses light splitting and disk tilting to quantify local stiffness, whereas P-SPOTs uses vertical disk displacement.

Results and Interpretation.

The spatial resolution and FOV C-SPOTs provides should be similar to P-SPOTs, meaning traction force and cell stiffness data from millions of interconnect cells spread across a 5×5 cm2 area can be simultaneously quantified in real-time. Calibration of color change sensitivity for different grating specifications and sizes on the C-SPOTs platform can establish a quantitative relationship between tilt angle and the amount of light detected in different colors. Video recording for rapid, dynamic measurements of cell mechanics is set by the collecting camera frame rates (~30 frames/sec for standard color CCD cameras).

Figure 9:
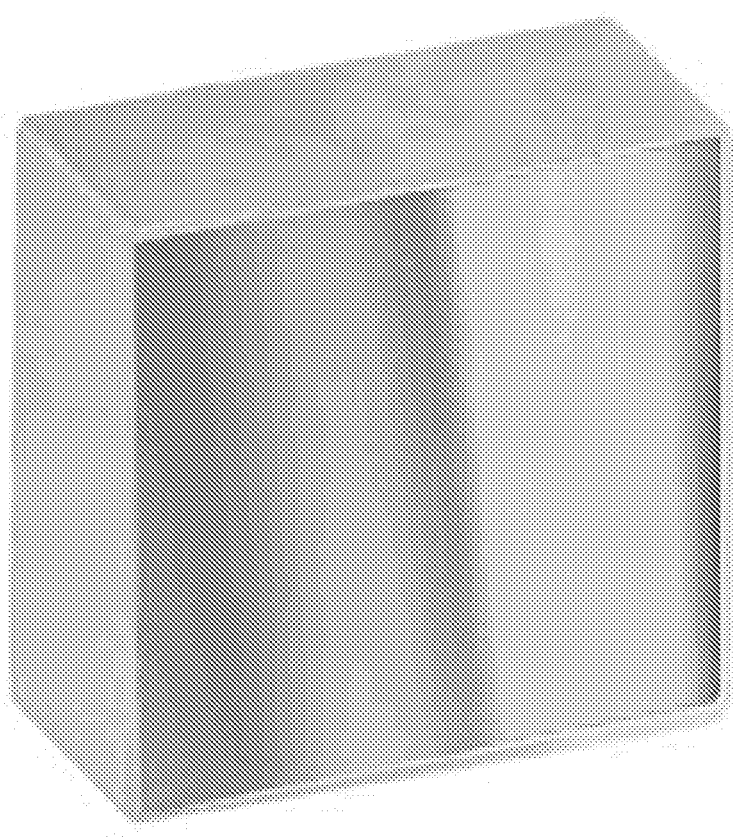
FIG. 9 shows a photograph of a 2.5×2.5 cm² optical diffraction grating element with 1200 grooves/mm captured by a typical CMOS camera.

When the concurrent monitoring area becomes large, it is believed the platform size will start to have some effect. Center wavelengths reflected by the grating mirrors in different regions on the platform are slightly different even without tilting. FIG. 9 shows an example of a large area effect from a standard optical grating element that is 2.5 cm in length. This potential confounder can be mitigated by setting different reference colors for zero-tilt conditions for control mirrors in different regions of the C-SPOTs platform.

Tuning P-SPOTs and C-SPOTs Performance in Multiple Independent but Interconnected Biological Systems Force sensing and propagation, along with chemical/ionic gradients and electrical impulses, within interconnected sheets/clusters of homogenous and heterogeneous cell types are fundamental organizing, actuating, and communications principles for multicellular metazoan organ systems. In certain embodiments engineered P-SPOTs and C-SPOTs can be used to quantify previously undiscoverable interactions and mechanical responses to external and internal perturbations in interconnected biological systems that are inaccessible to single cell response profiling technologies. In addition, subcellular resolution will reveal local cell compensations and heterogeneities and thereby provide superior understanding of the complexities within these systems compared to large thin film force averaging approaches, such as MTF. Various illustrative, but non-limiting uses are described below.

Force Generation During Pluripotent Stem Cell Differentiation to Beating Cardiomyocytes.

Dramatic morphologic changes occur in the appearance of mouse and human pluripotent stem cells (PSCs) as they are forced to differentiate over days into an electrically coupled sheet of cardiomyocytes (CMs). During this differentiation process, multiple niduses of pacemaker cells initiate periodic contractions that over time synchronize and propagate as rhythmic beating in a tissue culture dish, similar to the pulsatile contractions of the heart. The biological methods for converting PSCs into CMs are well established, highly reproducible (Bhattacharya et al. (2014) *J Vis. Exp.* 91: 52010), and provide an ideal physiologic testbed for P-SPOTs and C-SPOTs traction force propagation, spread, and quantification with each beat from initiating pacemaker cells. Once can seed PSCs onto matrigel coated P-SPOTs and C-SPOTs platforms at optimal densities and induce them to differentiate by Wnt signaling pathway stimulation. It is expected that on day 0, cells will be 100% confluent with compact morphology and minimal cell debris. On days 1-2, ~40% of cells will apoptose and die with the attached remaining viable cells retaining a compact morphology. These remaining cells will recover by day 4 and begin to replicate. At days 5-6, minimal cell death occurs and dense patches begin appearing. It is believed that by day 8 a confluent monolayer with compact morphology and interspersed dense patches with pacemaker cells arising from these dense patches that begin spontaneously contracting out of sync. By day 10, robust contractions and increased electrical signaling and contraction coordination should commence and continue to spread throughout the culture from that point onwards, accompanied by progressive acquisition of established CM biomarkers over the differentiation period.

This remarkable CM differentiation system can be used to collect data on localized cell stiffness (P-SPOTs) in PSCs, during earliest death-phase of differentiation (expect to lose local stiffness with kinetics similar to rate of cell death), proliferation phase, establishment of dense patches, initiation of contractions, spread of contractions, and coordinated rhythmic beating. C-SPOTs platforms can quantify traction force generation in the cell death, proliferation, beat initiation, spread, and coordination phases of CM monolayer establishment. Precise cell localization within the dish and easy visualization (e.g., cleared zone, viable non-beating cell, contracting cell) will provide initial validation for underlying P-SPOTs and C-SPOTs quantification of Young's modulus and traction force. Time lapse videography can be obtained from localized dense-patch beat establishment through coordinated beating of the CM monolayer to specific P-SPOTs and C-SPOTs quantification temporally. Individual cells can be spot-checked at different stages of differentiation (e.g. PSCs, dying phase, proliferating phase, dense patch phase, beating phase) by AFM by moving the platform to an AFM stage and standard contact mode stiffness measurements as further validation. The CM testbed and validating videography and AFM field-standard approaches can be used to fine-tune P-SPOTs and C-SPOTs technologies for a wide range of future applications in cell death, growth, and force initiation and propagation.

Force Generation During Reprogramming of Fibroblasts to Pluripotent Stem Cells:

The efficiency of reprogramming somatic cells to PSCs is generally low (~0.01-1.0%), depends upon initial cell type and conditions chosen, and involves many intermediate states until the endpoint (Takahashi & Yamanaka (2016) *Nat. Rev. Mol. Cell Biol.* 17: 183-193; Wong et al. (2017) *Curr. Opin. Chem. Eng.* 15: 95-101). Not all cells induced to reprogram to pluripotency survive the process or make it all the way to the endpoint and it is unclear which cells from biomarker and growth studies succeed in navigating this process. The well-established OSKM transcription factor reprogramming method, from commercially available human or mouse fibroblasts to PSCs, provides a second ideal testbed to evaluate the ability of P-SPOTs and C-SPOTs technologies to identify rare cells within complex mixtures that complete the reprogramming process to PSCs by their mechanical signature. In this case, the testbed is reversed and where, as described above, individual colonies generate a sheet of cells, instead a sheet of cells will yield individual colonies. Human and mouse fibroblast monolayers can be grown on P-SPOTs and C-SPOTs platforms and induced to differentiate into induced PSCs (iPSCs) by the OSKM method (Lowry & Plath (2008) *Nat. Biotechnol.* 26: 1246-1248; Lowry et al. (2008) *Proc. Natl. Acad. Sci. USA,* 105: 2883-2888; Nakagawa et al. (2008) *Nat. Biotechnol.* 26: 101-106; Takahashi et al. (2007) *Cell,* 131: 861-872; Takahashi & Yamanaka (2006) *Cell,* 126: 663-676). Videography and cell location can provide visual identification of potential candidates that survive the ~2 week reprogramming process. Simultaneous LCI quantification of initial biomass loss, expected for all fibroblasts that are either destined to die or to eventually generate an iPSC clone, followed by biomass stabilization, increase, and rapid cell divisions (Zangle et al. (2013) *Biophys. J.* 105: 593-601) can provide validation for P-SPOTs and C-SPOTs mechanical quantification to identify rare cells of interest within a sea of dying and incompletely reprogrammed cells.

Effect of Local Toxin or Excitation on Multicellular Mechanical Response Profile.

CM monolayers made on P-SPOTs and C-SPOTs platforms as described above can be used. Using a robotic micromanipulator arm outfitted with a delivery micropipette, a cardiotoxin (e.g. Adriamycin, aka doxorubicin, a DNA intercalating drug used in cancer therapy), a cardiac stimulant (e.g. epinephrine), and a cardiac suppressant (e.g. a beta-adrenergic blocking agent of which there are many to choose from) can be spot-applied. The local radiating and distal effects can be quantified instantaneously and temporally on cardiac contractility, traction force, and stiffness as a testbed for P-SPOTs and C-SPOTs technologies for distal tissue sheet damage or excitation and compensatory responses throughout the sheet. Simultaneous effects on cardiac contraction by $Ca^{2+}$ intracellular store release flux can be determined by fluorescence microscopy, which will enable further technical modalities in addition to LCI to complement and help validate P-SPOTs and C-SPOTs force actuating and quantifying platforms.

Local Force Application and Transmission to Distal Cells.

The embedded mirrors on P-SPOTs and C-SPOTs platforms are linearly responsive to magnet field strength, providing a mechanism for precise perpendicular, lateral, angular and rotational force applications depending on the positioning and strength of a piezo-controlled magnet relative to each platform. Unlike applications where force generation is an inherent biological property of the cell and system, in this application, local and transmitted forces of defined values can be evaluated on the P-SPOTs and C-SPOTS platforms. In a range of experiments, a CM monolayer and/or a fibroblast monolayer can be used. Illustrative testbed studies will include, but are not limited to, (A) activating a perpendicular force at one edge of the P-SPOTs platform with quantification of local and transmitted mechanical force and Ca2+ flux (for CM monolayers). (B) Activation of angular, lateral and rotational force at one edge of C-SPOTs platform with quantification of local and transmitted mechanical force and Ca2+ flux. (C) Patterned activation of perpendicular and/or lateral forces at specific locations or in timed sequences (e.g. an applied force gradient) within P-SPOTs and C-SPOTs platforms with quantification of local and transmitted mechanical force and Ca2+ flux. (D) Combined P-SPOTs and C-SPOTs actuation to evaluate combined effects of perpendicular and lateral forces with quantification of local and transmitted mechanical force and Ca2+ flux. These studies will help refine the capabilities of P-SPOTs and C-SPOTs platforms and assist in manufacturing adjustments (e.g. reflective mirror aspect ratios, embedded elastomer viscoelasticity) for quantifying known local and transmitted applied forces in cell sheets. Selected spot locations can be interrogated by LCI (Eldridge et al. (2017) *Biophys. J.* 112: 692-702) and AFM (Kandel et al. (2017) *J. R. Soc. Interface,* 14: 20170071) to quantify Young's modulus in comparative measurements to local P-SPOTs and C-SPOTs values as a validation check on precision, accuracy, and reproducibility.

BLAST Cell Engineering and SPOTs Analysis.

The capability for generating stable mitochondria transfer cell lines (French et al. (2011) *Proc. Natl. Acad. Sci. USA,* 108: 12095-12100; Wu et al. (2016) *Cell Metab.* 23: 921-929; Wu et al. (2011) *Anal. Chem.* 83: 1321-1327; Wu et al. (2010) *Opt. Express,* 18: 23153-23160) can be combined with P-SPOTs and C-SPOTs technologies to enable mechanical force generation measurements in cellular engineering. We have generated immortalized mouse embryonic fibroblasts (MEFs) that cannot respire because they lack mitochondrial DNA (mtDNA; so called rho-null or p0 cells) and have generated "rescued" respiration in these MEFs by BLAST transfer of mitochondria containing mtDNA from MDA-MB-231 breast carcinoma cells, as we have done before in a different cellular context (Wu et al. (2016) Cell Metab. 23: 921-929) (data not shown). Because MEF p0 and rescued cells have different energy generating capacities and can grow in extended sheets as described. Without being bound to a particular theory, it is believed they will have different abilities to propagate and transmit force, that can be quantified by P-SPOTs and C-SPOTs studies as described herein.

Furthermore, parental, mtDNA-containing MEFs and MDA-MB-231 mtDNA-containing MEFs can be reprogrammed to mouse PSCs by the OSKM approach and then evaluate differences in force generation can be evaluated when differentiating these iPSCs to CMs. The idea here is that mtDNA sequence differences between native MEF and MDA-MB-231 mtDNAs, which has been verified by sequencing (data not shown), will result in different CM monolayer respiratory capacities that can be confirmed by Seahorse XF96 flux assays using methods (Zhang et al. (2012) Nat. Protoc. 7: 1068-1085). It is believed this will result in differences in CM force generation, spread, and propagation that can be quantified by P-SPOTs and C-SPOTs technologies. It is also believed that local stimulation or damage to the CM monolayer, using cardiac toxins, stimulants, or suppressants as described above, can result in different patterns of CM monolayer force and $Ca^{2+}$ flux compensations between the native and MDA-MB-231 mtDNA modified CMs. Selected single cell validations can be performed within the CM sheet by AFM and LCI measurements. Overall, these studies can establish the ability for P-SPOTs and C-SPOTs technologies to quantify differences in force generation and propagation with subtle changes in bioenergetics and serve to link to our unique capabilities in large cargo transfer into cells and cell engineering technologies (Marx et al. (2014) Nat. Meth. 13: 37-40).

The P-SPOTs and C-SPOTs technologies as described herein are intended to interrogate the statistical sensitivity and specificity of the systems in a variety of biological settings. No particular biological problem is addressed in the examples described herein. Validation of the measurements described herein is of necessity using selected single-cell based spot methods using established current AFM and LCI technologies because no wide field, subcellular force-quantifying methods currently exist. This is the enabling technology that P-SPOTs and C-SPOTs approaches provide for a huge swath of future biological investigations.

The biological systems used for the tests described herein are all well-established and in operation within our laboratories. It is believed that no alternative approaches exist to the wide-field instantaneous mechanical force profiling studies that P-SPOTs and C-SPOTs technologies portend. This is the innovative nature of our proposed technology platforms. Results of various measurements can enable refinement of optical mirror size and aspect ratios. Additionally the Young's modulus elastomers in which the mirrors are embedded can be refine and optimized as well as tracking and analytic MATLAB software for quantitative phase microscopy that is the basis for LCI and that we have generated over many years of studies (Reed et al. (2011) Biophys. J. 101: 1025-1031; Zangle & Teitell (2014) Nat. Meth. 11: 1221-1228; Reed et al. (2008) Nanotechnology 19: 235101; Reed et al. (2008) ACS Nano, 2: 841-846; Chun et al. (2012) Analyst, 137: 5495-5498; Kim et al. (2015) J. Biomed. Opt. 20: 111211; Zangle et al. (2013) PLoS One, 8: e68916; Zangle et al. (2014) PLoS One, 9: e115726).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A device for the measurement of mechanical properties of cells or other moieties, said device comprising:
   a transparent elastic or viscoelastic polymer substrate disposed on a rigid transparent surface, where said polymer substrate is substantially flat and continuous;
   a plurality of micromirrors disposed on or in said polymer substrate, wherein each micromirror comprises a reflective surface that is oriented substantially parallel to the surface of said polymer substrate, and wherein said micromirrors each comprises a 2-D optical diffraction grating disposed on said reflective surface, and each of said micromirrors is a rigid and flat even when said polymer substrate is deformed by pressing.

2. The device of claim 1, wherein said micromirrors comprise a surface coated with a magnetic or ferromagnetic material.

3. The device of claim 2, wherein said micromirrors comprise a ferromagnetic material selected from the group consisting of iron, nickel, cobalt, and alloys thereof.

4. The device of claim 1, wherein said diffraction grating(s) comprise from about 600, or from about 700, or from about 800 up to about 2000 grooves/mm, or from about 1,000 up to about 1600 grooves/mm, or from about 1100 up to about 1300 grooves/mm, or about 1200 grooves/mm.

5. The device of claim 1, wherein the thickness of said polymer is selected to effectively decouple tilting behaviors of neighboring mirrors.

6. The device of claim 1, wherein:
   the Young's modulus (E) of the polymer is about the stiffness of a typical mammalian cell; and/or
   the Young's modulus (E) of the polymer ranges from about 1 kPa to about 40 kPa.

7. The device of claim 1, wherein:
   said device comprises at least 1,000 micromirrors, or at least 10,000 micromirrors, or at least 100,000 micromirrors, or at least 1,000,000 micromirrors, or at least 5,000,000 micromirrors, or at least 10,000,000 micromirrors; and/or
   the distance between neighboring mirrors ranges from about 5 µm, or from about 10 µm, or from about 20 µm, or from about 30 µm, or from about 40 µm, or from about 50 µm up to about 200 µm, or up to about 150 µm, or up to about 100 µm; and/or
   said micromirrors are present at a density of at least about 1 million micromirrors/25 $cm^2$, or at least about 5 million micromirrors/25 $cm^2$, or at least about 10 million micromirrors/25 $cm^2$; and/or
   said micromirrors have a maximum dimension normal to the reflective face of less than about 50 µm, or less than about 40 µm, or less than about 30 um, or less than about 20 µm, or range in size from about 1 µm or from about 3 µm or from about 5 µm up to about 30 µm, or up to about 25 µm, or up to about 20 um, or up to about 10 µm; and/or said micromirrors have a maximum dimension normal to the reflective face ranging from about 5 µm to about 20 µm; and/or said micromirrors have a maximum dimension normal to the reflective face ranging from about 5 µm to about 20 µm; and/or said micromirrors have a maximum dimension normal to the reflective face ranging from about 5 µm to about 10 µm.

8. The device of claim 1, wherein:

said micromirrors are circular, ovoid, square, rectangular, or an irregular polygon; and/or said micromirrors have an aspect ratio ranging from about 1 up to about 20; or said micromirrors have an aspect ratio of about 1; or said micromirrors are substantially circular.

9. The device of claim 1, wherein the thickness of said micromirrors ranges from about 1 µm, or from about 5 µm, or from about 10 µm up to about 50 µm, or up to about 40 µm, or up to about 30 µm, or up to about 20 µm, or up to about 15 µm.

10. The device of claim 1, wherein:

said micromirrors have an index of refraction at least twice the index of refraction of said polymer substrate; and/or said micromirrors comprises a material selected from the group consisting of silicon, gallium arsenide, gallium phosphide, and germanium.

11. A system for quantifying mechanical interactions in multicellular biological systems, said system comprising:

a device according to claim 1; and a broadband light source that is collimated and illuminates the reflective surface and diffraction grating of said micromirrors.

12. The system of claim 11, wherein said system uses two orthogonal broadband light sources.

13. The system of claim 11, wherein:

said system comprises a low N.A. lens with a small detection angle to pick up a narrow band of light reflected from said micromirrors;

said system further comprises a CCD camera disposed to detect a different and distinguishable color(s) as said micromirrors tilt; and/or said system is configured to utilize a single pixel to detect tiling of a mirror.

14. A method of quantifying mechanical properties and/or interactions in multicellular biological systems, said method comprising:

providing a plurality of cells on the surface the viscoelastic polymer in a system according to claim 11; and detecting the color of light reflected from said micromirrors to provide a measure of the orientation of said micromirrors and to provide measures changes in micromirror position indicating the mechanical properties of cells comprising said system.

15. The method of claim 1, wherein said micromirrors are fabricated from a material selected from the group consisting of silicon, gallium arsenide, gallium phosphide, germanium, and glass.

16. The method of claim 15, wherein said micromirrors are fabricated from silicon.

\* \* \* \* \*